United States Patent [19]

Grylls et al.

[11] 4,081,558

[45] Mar. 28, 1978

[54] PROCESSES AND APPARATUS FOR PRODUCING ACTIVE DRIED YEAST

[75] Inventors: Frederick S. M. Grylls, Morden, England; Stanley D. Rennie, Menstrie; Michael Kelly, Stirling, both of Scotland

[73] Assignee: The Distillers Company (Yeast) Limited, Morden, England

[21] Appl. No.: 716,055

[22] Filed: Aug. 20, 1976

[30] Foreign Application Priority Data

Aug. 22, 1975 United Kingdom ............... 34862/75

[51] Int. Cl.$^2$ ............................................. C12C 11/30
[52] U.S. Cl. ..................................... 426/62; 34/57 A; 195/74; 195/98; 426/465; 426/473
[58] Field of Search .................... 426/62, 60, 465, 467, 426/473; 34/57 A, 57 R; 195/74, 98

[56] References Cited

U.S. PATENT DOCUMENTS 3,063,848  11/1962  Van Gelder .......................... 426/467
3,885,049  5/1975  Taylor ..................................... 426/62

*Primary Examiner*—R. B. Penland
*Attorney, Agent, or Firm*—Lawrence Rosen; E. Janet Berry

[57] ABSTRACT

A process is described of making active dried yeast comprising drying crumbly yeast aggregates in a fluidized bed and, during the fluid bed drying, and before the yeast has a dry matter content of 80%, subjecting the aggregates to disintegration forces while they are fluidized and while the dry matter content of the yeast is from 50 to 70%, the disintegration forces being sufficient to break the aggregates down into powder but insufficient to break the yeast cells themselves.

11 Claims, 1 Drawing Figure

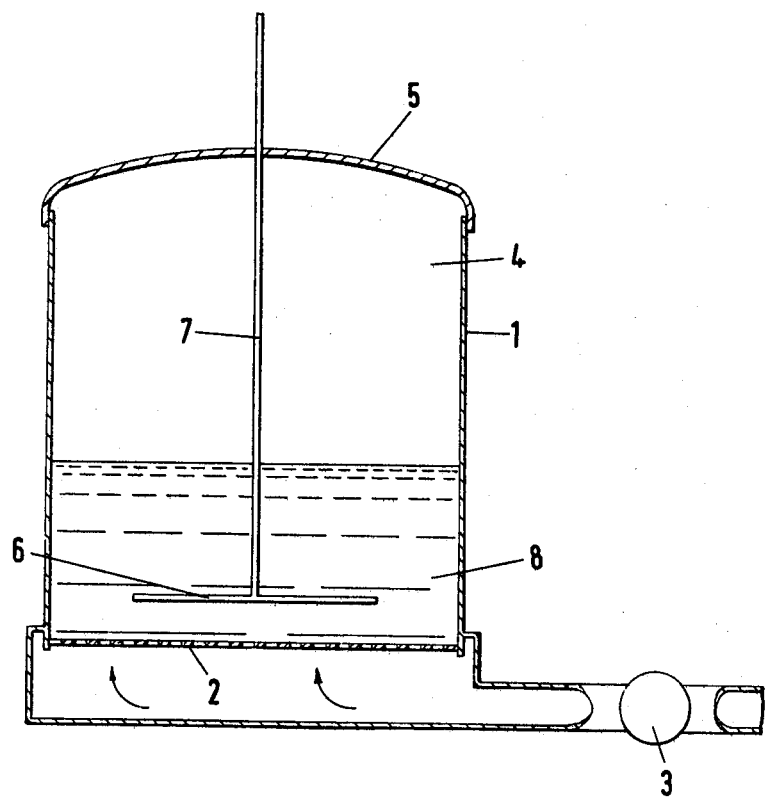

PROCESSES AND APPARATUS FOR PRODUCING ACTIVE DRIED YEAST

Active dried yeast is well known and is made by drying particles of moist yeast until the dry matter content is, for example, from 90 to 97%. It is well known that the drying conditions significantly affect the final activity of the yeast. Traditionally active dried yeast has generally been made by drum drying, as a result of which the product is in the form of pellets, and these have a rather hard surface structure and a substantial proportion of them are rather large, for example having a minimum dimension of 1, or more usually, 2 mm or more. More recently processes for making active dried yeast in powder form have been known. In these the yeast particles are smaller than in pellet yeast, for example generally having a minimum dimension of less than 1 mm, and are not so hard as in pellet yeast. Generally the methods involve forming small moist particles and then drying these by one of various methods, a preferred method being fluidised bed drying. We use this term to encompass any method in which the particles are held in a bed and are at least partially entrained in the drying gas.

One particularly satisfactory method of making active dried yeast is described in our British patent specification No. 1,369,551. In this crumbly yeast is fed continuously into a mill through which air is passed and is disintegrated in the mill to a powder, the powder is continuously carried out of the mill in a stream of air, and is then dried in for instance a fluidised bed, the drying being conducted in the substantial absence of any force tending to compress the powder, at least until the dry matter content exceeds 75% by weight.

Another method is described in our specification No. 1,196,786, and comprises spray drying a cream to form moist particles and then drying them to powdered active dried yeast. Thus most at least of the methods of making powdered active dried yeast (as opposed to pellet active dried yeast) involve two separate steps, namely the formation of moist particles having particle size of the order of that required in the dried yeast, and then the drying of these particles.

A single stage method is known, namely by spray drying a yeast cream to form a powder having a dry matter content of 90% or more in a single step, but spray dried products of this type tend to have rather poor activity.

Our object has been to avoid the need to make very small particles of moist yeast, and instead to make powdered active dried yeast by a simpler process than heretofore.

According to the invention powdered active dried yeast is made by a process comprising drying crumbly yeast aggregates in a fluidized bed, and, during the fluid bed drying, and before the yeast has a dry matter content of 80%, subjecting the aggregates to disintegration forces while they are fluidized, the disintegration forces being sufficient to break the aggregates down into powder but insufficient to break the yeast cells themselves.

The crumbly yeast aggregates can have any dry matter content typical of yeast in the crumbly state, and as known this is generally between 27 and 40%, preferably 30 to 40%.

The aggregates can be of any convenient shape or size provided they are capable of being fluidized. Thus they will generally have a minimum dimension greater than 1 mm and it can be, for instance, greater than 3 or 5 mm, for instance as much as 1 cm. They do not have to be of regular size, and indeed in the simplest embodiment can be made simply by crumbling compressed yeast manually. Alternatively any convenient method of comminuting compressed yeast to achieve a similar effect can be used.

A particularly convenient method of carrying out the invention is to extrude the yeast using a low pressure extrusion device, for instance one which is or has the same action as a domestic mincer. Conveniently this gives rod-shaped particles having a diameter of, say, 3 to 8 mm and a length of, say, 5 to 15 mm.

Since the size of the yeast particles will change substantially during the drying process it may be necessary to regulate the rate of flow of fluidizing air or other gas appropriately during the process in order to compensate for this.

It is easily possible in the invention to produce active dried yeast particles substantially all of which have a minimum dimension less than 1 mm and usually less than 0.6 mm, for instance 0.35 mm or below. Thus not only does the method of the invention result in the production of powdered active dried yeast particles in a single stage from large aggregates but also it produces particles of a very uniform small size, whereas a fluidized bed drying technique such as is described in specification No. 1,369,551 may result in a significant proportion, at least 10% and sometimes as much as 40 or 50% by weight, of the particles having a particle size greater than is desired.

It is essential in the invention that the yeast is subjected to disintegration forces while it is fluidised, that is to say while it is at least partially entrained in drying air or other fluidizing gas, and that at least during the time the yeast passes through the sticky stage it should not be allowed to go into a non-fluidized state.

It is well known that while yeast is being dried it passes through the so-called "sticky stage" during which it has a very high tendency to agglomerate to itself. This sticky stage occurs at dry matter contents between about 50 and about 70 or 80%. Because of the sensitivity and high tendency to agglomerate of yeast particles as they pass through this stage, it is known that great care has to be exercised in handling them at this stage.

The subjection of the yeast to disintegration forces during the fluidized bed drying can be conducted throughout the drying process but it appears that there are no advantages, and there may be some disadvantages, for instance in loss of activity, if the yeast is subjected to disintegration forces at near the end of the fluidized bed drying, for instance after it has a dry matter content of about 80–85%. It is essential, therefore, that it be subjected to disintegration forces at some stage before it acquires a dry matter content of 80%, and preferably before it acquires a dry matter content of 70%. There may be no advantage if it is subjected to some or all of the disintegration forces too early in the drying stage, and so preferably some at least of the application of disintegration forces is conducted after the yeast have a dry matter content of 50%. It often is desirable that the yeast should be subjected to disintegration forces intermittently or, preferably, continuously, throughout most at least of the time they are in the sticky stage, i.e., a dry matter content of 50 to 70 or 80%, and usually from the start of drying to 70 or 80% dry matter content.

Expressed another way, it appears desirable that the yeast be subjected to disintegration forces at least during the first and/or the second quarters of the total drying time, and conveniently it is subjected to the forces during the third quarter of the drying time as well.

The total drying time depends on the rate, temperature and humidity of the drying air or other gas but is generally ¼ to 4 hours, e.g., 1 to 2½ hours. The gas temperature is generally less than 120° C, e.g., 32 to 55° C, the yeast temperature preferably being maintained below 55° C, most preferably below 45° C. The relative humidity of the gas is preferably below 45° at 20° C, especially 35%.

In the simplest method the yeast is subjected to the forces while it remains in the fluidized bed in which it is being dried. With such an arrangement it is desirable that the disintegration forces be applied for a prolonged period of time, within the relevant periods mentioned above, so as to ensure that all yeast has the opportunity of being subjected to the forces. However, the yeast may be subjected to the disintegration forces outside the fluidized bed. For instance yeast may be taken, whilst fluidized, from the bed and passed through suitable disintegration means whilst it is still at least partially entrained in air or other fluidizing medium and recycled to the bed, or it may be passed on to a different fluidized bed in which it is further dried.

In one continuous method of drying, moist yeast is fed to a first fluidized bed in which it is dried to a predetermined moisture content, is transferred in an entraining gas stream to a second fluidized bed in which it is dried to a further predetermined moisture content and so forth until it has the desired moisture content, and during at least one of the transfer steps it is subjected to the said disintegration forces. Naturally when the yeast is subjected to the disintegration forces only for a short time, as when it is taken out of a bed and fed back into it or into another one, it is necessary that it should have a moisture content of between 50 or 60 and 70 or 80% so as to obtain the maximum benefit from the disintegration step.

In view of the known properties of yeast as it passes through the sticky stage, it is highly surprising that far from being positively harmful to subject the yeast to disintegration forces while it is drying in a fluidized bed drying process, the method of the invention is in fact highly advantageous.

The disintegration forces combined with the effect of the fluidized bed clearly break the yeast aggregates down into smaller particles having the desired final particle size and additionally prevent these particles aggregating back into larger particles, as happens if no precautions are taken during the fluidized bed drying of small moist yeast particles. It is not clear whether the forces act upon these aggregates of partially dried particles to disintegrate them back into the desired fianl particle size or whether they act upon the particles of desired size in some way so as to prevent them aggregating back into larger particles, but probably it is a process of continuous disaggregation, aggregation and disaggregation of small but discrete particles during the sticky stage. Whatever the mechanism, it is easily possible so to chose the disintegration forces as to achieve the desired particle size. Put simply, if the disintegration forces are not great enough the dried particles will be larger than is desired but if they are too great the dried particles will have poor activity, probably because the yeast cells themselves have been broken down.

Any means of providing disintegration forces that is capable of providing the very easily obtained balance between excessive and insufficient force can be used. One method of providing the disintegration forces is to subject the yeast to the effect of very high gas velocities either in the fluidized bed or in a duct leading out of the fluidized bed and either back into that bed or onto another bed. Such high velocity gas streams may be provided either by directing gas jets into the duct or fluidized bed or by passing a stream of yeast entrained in gas through a suitable accelerating device, such as a venturi. The disintegration forces may also be provided in the duct or bed by bursting gas bubbles produced by chemical reaction or pressure reduction. Preferably, however, the disintegration forces are provided by mechanical disintegrating means, although these may in fact bring about disintegration primarily as a result of high gas velocities close to their solid surfaces giving rise to explosive disintegration of large yeast particles, rather than as a result of impact between the solid surfaces and the yeast. Suitable mechanical disintegration means include one or more members that rotate or oscillate at high speed. It is preferred that part at least of the or each member moves at a speed greater than 200, preferably greater than 500, and most preferably greater than 1,000 feet per minute. Speeds of 1,500 to 3,000 or 4,000 feet per minute are often very satisfactory. Sometimes if the speed is considerably higher, for example greater than 5,000 feet per minute and especially if it is greater than 10,000 feet per minute the activity of the yeast may be seriously affected.

Oscillating members such as cutter bars, other bars or sieves may vibrate with such speeds whilst rotating members, such as blades, rods or discs, may rotate at a speed such that at least the outer half of the blade diameter has such a rotational velocity. Normally they rotate at a speed such that the outer peripheral velocity is as indicated above. For instance, a blade or rod, e.g., 2.5 inches in diameter, conveniently rotates in the fluidized bed of particles at between 2,000 and 6,000 rpm, e.g., 3300—5500 r.p.m. with best results being obtained at about 4,000 to 5,000 rpm. The free spinning speeds are of course generally higher. Generally any disintegrating means that is a rotating member will rotate at at least 500, and usually at least 1000, rpm, and preferably at the figures given above, and so clearly the invention is providing something more than mere stirring of the bed, e.g., to improve heat transfer.

If the disintegration forces are applied in the fluidized bed they may be provided by a single mechanical disintegrator, in which event it will generally operate over at least a third of the area of the bottom of the bed and be positioned substantially centrally, or they may be provided by a plurality of mechanical disintegrators together operating over at least a third of the bed, some at least of which will generally be positioned around the periphery of the bed. For instance there may be a plurality of rotating blades, rods or discs positioned around the bed. The mechanical disintegrator can be positioned at any height where the yeast is in a fluidized (as defined above) condition, but preferably is close to the base of the bed and is indeed generally in the bottom part of the bed.

Thus it may be in the bottom half of the depth of the bed when fluidized and preferably in the bottom quarter. It is often preferred for it to be less than 2, and most preferably less than 1, e.g., ½ or less, inches above the base of the bed.

Blades, rods or bars used in a mechanical disintegrator may be of simple rectangular or circular cross section, but blades may have a pitch, that is to say they should be twisted out of the horizontal.

Especially when the disintegrating forces are applied by a central rotor, or by several rotors, it is often desirable to provide in the fluidized bed means for urging particles at the periphery of the bed towards the center of the bed, so as to counteract any tendency for particles to accumulate at the periphery due to centrifugal action of the one or more rotors. Such means may comprise a member, for instance a rotor blade, that slowly moves around the periphery of the bed forcing the yeast towards the center of the bed. Thus a preferred apparatus comprises a slowly rotating (e.g., 2 to 50 or 100, preferably 10 to 20, rpm) rotor blade that sweeps the periphery of the bed and one or more fast rotating blades. For instance a single coaxial shaft may drive, at about the same level in the bed, a small diameter disintegrating rotor and a large diameter sweeping blade.

The fluidized bed used in the invention may be of otherwise conventional construction. Thus as shown diagrammatically in the accompanying drawing of an example of such a bed it will comprise a housing 1 having a perforated base 2 up through which air of other heated fluidizing gas can be pumped from pump 3 and an outlet 4 at the top for the escape of waste gas covered generally by a filter, for example a filter bag 5, to prevent the loss of fine particles with the escaping air. A stirrer rod 6 or other mechanical disintegrating means carried on a rotatable shaft 7 is positioned in the bed 8 of yeast (shown in the fluidized state) at an appropriate height or in a duct leading from that bed. Such apparatus is included within the scope of the invention.

It is preferred that the yeast should contain a wetting agent, for example as described in British patent specification No. 1,132,793. Most preferably the yeast contains a mixture of sorbitan fatty acid esters, for example a 1 to 1 mixture of the products known as "Span 40" and "Span 60." The amount of wetting agent is usually below 3%, for example 0.5 to 2%, based on the dry weight of the yeast. Conveniently it is added either to the yeast cream or to the compressed yeast or to the crumbly yeast aggregates.

The following are Examples of how the invention may be performed. They may be conducted in a laboratory scale fluidized bed container 6 inches high having an internal diameter at the top of 6 inches and having at the base a 1 inch reinforcement ring giving an internal diameter of 4 inches.

EXAMPLE 1

Compressed yeast treated with 0.5% by weight of a 1:1 mixture of Span 40® and Span 60® which trademark materials are described in U.S. Pat. No. 3,962,467 column 3 lines 37–57, incorporated herein by reference and made in conventional manner may be crumbled by hand into irregular aggregates having dimensions of the order of 2 to 8 mm, the yeast having a moisture content of about 32% dry matter. These rough aggregates may be charged into the drier and air having a temperature of about 45° C may be pumped up through the bed, sufficient to maintain the fluidized state, for about 2 hours. At the start of the process the outlet air temperature may be about 20° to 22° C but may be about 43° to 44° C at the end of the drying process. Throughout, for instance, the first three-quarters of the drying process a four bladed rotor, each blade being 1.25 inches in length from the shaft center to the outer tip of the blade and which is positioned in the bottom half of the bed, may be rotated by a motor above the rotor at a speed of 4,400 r.p.m. The blade may conveniently have a pitch of between 3 and 7 mm.

The product is found to be active dried yeast substantially all of which passes through a mesh size of 0.35 mm and which has good activity as measured by conventional fermentometer volume and bakery proof time tests.

EXAMPLE 2

The process of Example 1 may be repeated in the same manner except that instead of crumbling the compressed yeast manually it may be extruded under low pressure by means of a conventional domestic mixer to give rod-shaped pieces of yeast having a diameter about 6 mm and a length about 9 mm. Similar satisfactory results are obtained.

EXAMPLE 3

The process of Example 1 may be repeated using, instead of the blade, a single horizontal rod that was rotated about a central vertical axis at 4400 rpm, giving a peripheral speed of 2900 fpm, with a gap of ¼ to ⅛ inch between it and the base of the bed from the start of the drying until the dry matter content was 80 to 85%. If desired a blade profiled to sweep yeast from the outside of the bed to the center may rotate at 15 rpm on the same shaft as the rod through appropriate gearing.

We claim:

1. A method of making powdered active dried yeast comprising drying crumbly yeast aggregates in a fluidized bed, and, during the fluidized bed drying, and before the yeast has a dry matter content of 80%, subjecting the aggregates to disintegration forces while they are fluidized, the disintegration forces being applied continuously or intermittently throughout the time the dry matter content of the yeast is from 50 to 70% and said distintegration forces being sufficient to break the aggregates down into powder but insufficient to break the yeast cells themselves said dried powder particles substantially all pass through a sieve having a mesh size of 0.35mm.

2. A method according to claim 1 in which the disintegration forces are provided by mechanical disintegration means comprising one or more members that rotate or oscillate at a speed such that part of said members moves at a speed greater than 200 feet per minute.

3. A method according to claim 2 in which part of said members moves at a speed of 1000 to 5000 feet per minute.

4. A method according to claim 2 in which said members rotate at least 2000 rpm.

5. A method according to claim 4 in which said members rotate at 4000 to 5000 rpm.

6. A method according to claim 2 in which the one or more members together operate over at least a third of the area of the bed.

7. A method according to claim 2 in which the one or more members are in the bottom half of the bed of yeast particles when fluidised.

8. A method according to claim 2 in which the disintegration forces are applied continuously in the fluidized bed in which the yeast is being dried during at least the first and/or second quarters of the total drying time.

9. A method according to claim 2 in which the yeast has a dry matter content initially of 27 to 40% and finally of 90 to 97%, and the drying is conducted for ¼ to 4 hours.

10. A method according to claim 2 in which the aggregates have a minimum dimension at least 3 mm in size.

11. A method according to claim 10 in which the aggregates are rod shaped and have been formed by extrusion.

* * * * *